US00PP29590P3

(12) United States Plant Patent
Beekenkamp

(10) Patent No.: US PP29,590 P3
(45) Date of Patent: Aug. 14, 2018

(54) ***CELOSIA* PLANT NAMED 'BKCELANP'**

(50) Latin Name: *Celosia plumosa*
Varietal Denomination: BKCELANP

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 52 days.

(21) Appl. No.: 14/999,801

(22) Filed: Jun. 28, 2016

(65) Prior Publication Data

US 2017/0374782 P1 Dec. 28, 2017

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Keith O Robinson
(74) *Attorney, Agent, or Firm* — C. A. Whealy

(57) ABSTRACT

A new and distinct cultivar of *Celosia* plant named 'BKCELANP', characterized by its broadly upright plant habit; moderately freely branching habit; freely flowering habit; bright pink-colored flowers arranged on narrow conical compound spikes; and good interiorscape and garden performance.

2 Drawing Sheets

Botanical designation: *Celosia plumosa.*
Cultivar denomination: 'BKCELANP'.

BACKGROUND OF THE INVENTION

The present invention relates to a new and distinct *Celosia* plant, botanically known as *Celosia plumosa* and hereinafter referred to by the name 'BKCELANP'.

The new *Celosia* plant is a product of a planned breeding program conducted by the Inventor in Maasdijk, The Netherlands. The objective of the breeding program is to create new *Celosia* plants that have unique and attractive flowers, long flowering period and good interiorscape and garden performance.

The new *Celosia* plant originated from an open-pollination in June, 2012 in Maasdijk, The Netherlands of *Celosia plumosa* 'BKCELFLM', disclosed in U.S. Plant Pat. No. 27,843, as the female, or seed, parent with an unknown selection of *Celosia plumosa* as the male, or pollen, parent. The new *Celosia* plant was discovered and selected by the Inventor as a single flowering plant from within the progeny of the stated open-pollination in a controlled environment in Maasdijk, The Netherlands in July, 2013.

Asexual reproduction of the new *Celosia* plant by terminal vegetative cuttings in a controlled environment in Maasdijk, The Netherlands since April, 2014 has shown that the unique features of this new *Celosia* plant are stable and reproduced true to type in successive generations.

SUMMARY OF THE INVENTION

Plants of the new *Celosia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BKCELANP'. These characteristics in combination distinguish 'BKCELANP' as a new and distinct *Celosia* plant:

1. Broadly upright plant habit.
2. Freely branching habit.
3. Freely flowering habit.
4. Bright pink-colored flowers arranged on narrow conical compound spikes.
5. Good interiorscape and garden performance.

Plants of the new *Celosia* differ from plants of the female parent, 'BKCELFLM', in the following characteristics:

1. Plants of the new *Celosia* are shorter than plants of 'BKCELFLM'.
2. Leaves of plants of the new *Celosia* are lighter green in color than leaves of plants of 'BKCELFLM'.
3. Plants of the new *Celosia* and 'BKCELFLM' differ in flower color as plants of 'BKCELFLM' have purple-colored flowers.

Plants of the new *Celosia* can be compared to plants of *Celosia plumosa* 'Kelos Purple', not patented. In side-by-side comparisons, plants of the new *Celosia* differ primarily from 'Kelos Purple' in the following characteristics:

1. Leaves of plants of the new *Celosia* are lighter green in color than leaves of plants of 'Kelos Purple'.
2. Plants of the new *Celosia* flower earlier than plants of 'Kelos Purple'.
3. Plants of the new *Celosia* and 'Kelos Purple' differ in flower color as plants of 'Kelos Purple' have purple-colored flowers.

BRIEF DESCRIPTION OF THE PHOTOGRAPHS

The accompanying colored photographs illustrate the overall appearance of the new *Celosia* plant showing the colors as true as it is reasonably possible to obtain in colored reproductions of this type. Colors in the photographs may differ slightly from the color values cited in the detailed botanical description which accurately describe the colors of the new *Celosia* plant.

The photograph on the first sheet comprises a side perspective view of a typical flowering plant of 'BKCELANP' grown in a container.

The photograph on the second sheet is a close-up view of typical inflorescences and the upper and lower surfaces of leaves of 'BKCELANP'.

DETAILED BOTANICAL DESCRIPTION

The aforementioned photographs and following observations, measurements and values describe plants grown in 12-cm containers during the spring in a glass-covered greenhouse in Maasdijk, The Netherlands and under commercial cultural practices typical of *Celosia* production. During the production of the plants, day temperatures ranged from about 17° C. to 18° C. and night temperatures ranged from about 16° C. to 17° C. Plants were pinched one time and were ten weeks old when the photographs and description were taken. In the following description, color references are made to The Royal Horticultural Society Colour Chart, 2015 Edition, except where general terms of ordinary dictionary significance are used.

Botanical classification: *Celosia plumosa* 'BKCELANP'.

Parentage:

*Female, or seed, parent.*—*Celosia plumosa* 'BKCELFLM', disclosed in U.S. Plant Pat. No. 27,843.

*Male, or pollen, parent.*—Unknown selection of *Celosia plumosa*, not patented.

Propagation:

*Type.*—By terminal vegetative cuttings.

*Time to initiate roots, summer.*—About 16 days at temperatures ranging from about 19° C. to 21° C.

*Time to initiate roots, winter.*—About 19 days at temperatures ranging from about 19° C. to 21° C.

*Time to produce a rooted young plant, summer.*—About 21 days at temperatures ranging from about 19° C. to 21° C.

*Time to produce a rooted young plant, winter.*—About 23 days at temperatures ranging from about 19° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant form and growth habit.*—Herbaceous annual typically grown as a potted plant; broadly upright plant habit; broadly obovate in overall shape; freely branching habit with about five lateral branches developing per plant; moderately vigorous growth habit.

*Plant height, soil level to top of foliar plane.*—About 17 cm.

*Plant height, soil level to top of floral plane.*—About 23.5 cm.

*Plant width (spread).*—About 25.9 cm.

*Lateral branches.*—Length: About 11.7 cm. Diameter: About 5 mm. Internode length: About 1.4 cm. Strength: Moderately strong. Aspect: About 37.5° from vertical. Texture and luster: Smooth, glabrous; axillary ribbed; slightly glossy. Color, developing and fully developed: Close to 68D lightly tinged with close to 145D; ribs, close to 67C.

Leaf description:

*Arrangement.*—Alternate; simple.

*Length.*—About 10.4 cm.

*Width.*—About 5 cm.

*Shape.*—Ovate.

*Apex.*—Apiculate.

*Base.*—Attenuate.

*Margin.*—Entire.

*Texture and luster, upper surface.*—Slightly rugose, glabrous; slightly glossy.

*Texture and luster, lower surface.*—Slightly rugose, glabrous; moderately glossy.

*Venation pattern.*—Pinnate.

*Color.*—Developing leaves, upper surface: Close to 143A. Developing leaves, lower surface: Close to 138B. Fully expanded leaves, upper surface: Close to 147A; towards the margins, tinged with close to N186C; venation, close to 187C to 187D. Fully expanded leaves, lower surface: Close to 148C; venation, close to 184A to 184C.

*Petioles.*—Length: About 2.7 cm. Diameter: About 3 mm. Texture and luster, upper and lower surfaces: Smooth, glabrous; moderately glossy. Color, upper surface: Close to N148D; towards the edges, close to 187D. Color, lower surface: Close to 177C; towards the edges, close to 185A.

Flower description:

*Flower type and arrangement.*—Single rotate flowers arranged in narrow conical terminal compound spikes; flowers face upright to outwardly.

*Flowering habit.*—Freely flowering habit with about 4,000 flowers developing per plant.

*Fragrance.*—None detected.

*Natural flowering season.*—Plants begin flowering about 70 days after planting; flowering continuous from spring into the autumn in The Netherlands.

*Postproduction longevity.*—Inflorescences of the new *Celosia* have good longevity and plants maintain good substance for about 40 days; flowers persistent.

*Inflorescence height.*—About 10.1 cm.

*Inflorescence diameter.*—About 6.4 cm.

*Flower diameter.*—About 6 mm.

*Flower height.*—About 6 mm.

*Flower buds.*—Length: About 6 mm. Diameter: About 1.5 mm. Shape: Lanceolate. Texture and luster: Smooth, glabrous; glossy. Color: Close to 71D.

*Petals.*—None observed.

*Sepals.*—Quantity and arrangement: Typically eight per flower arranged in about two whorls. Length: About 6.5 mm. Width: About 1.5 mm. Shape: Lanceolate. Apex: Narrowly acute. Base: Obtuse. Margin: Entire. Texture and luster, inner and outer surfaces: Smooth, glabrous; glossy. Color: When opening, inner and outer surfaces: Close to 72C to 72D. Fully opened, inner and outer surfaces: Close to 72D; venation, close to 72C to 72D; color does not change with development.

*Peduncles.*—Length: About 9.6 mm. Diameter: About 4 mm. Angle: Upright to about 65° from vertical. Strength: Moderately strong. Texture and luster:

Smooth, glabrous; slightly glossy. Color: Close to N148D slightly tinged with close to 68D.

*Pedicels*.—Length: About 0.5 mm. Diameter: About 0.5 mm. Angle: About 80° from peduncle axis. Strength: Moderately strong. Texture and luster: Smooth, glabrous; slightly glossy. Color: Close to 71D.

*Reproductive organs*.—Stamens: Quantity per flower: Five. Filament length: About 4 mm. Filament color: Close to 65B to 65C. Anther size: About 0.3 mm by 1 mm. Anther shape: Narrowly oblong. Anther color: Close to 64A. Pollen amount: Moderate. Pollen color: Close to 156D. Pistils: Quantity per flower: One. Length: About 4 mm. Stigma diameter: About 1 mm. Stigma shape: Club-shaped, three-parted. Stigma color: Close to 64A. Style length: About 3.5 mm. Style color: Close to 61B. Ovary color: Close to 65D.

*Seeds and fruits*.—Seed and fruit development have not been observed on plants of the new *Celosia*.

Disease & pest resistance: Plants of the new *Celosia* have not been observed to be resistant to pathogens and pests common to *Celosia* plants.

Garden performance: Plants of the new *Celosia* have been observed to have good garden performance and to be suitable for USDA Hardiness Zones 9 to 12.

It is claimed:

1. A new and distinct *Celosia* plant named 'BKCELANP' as illustrated and described.

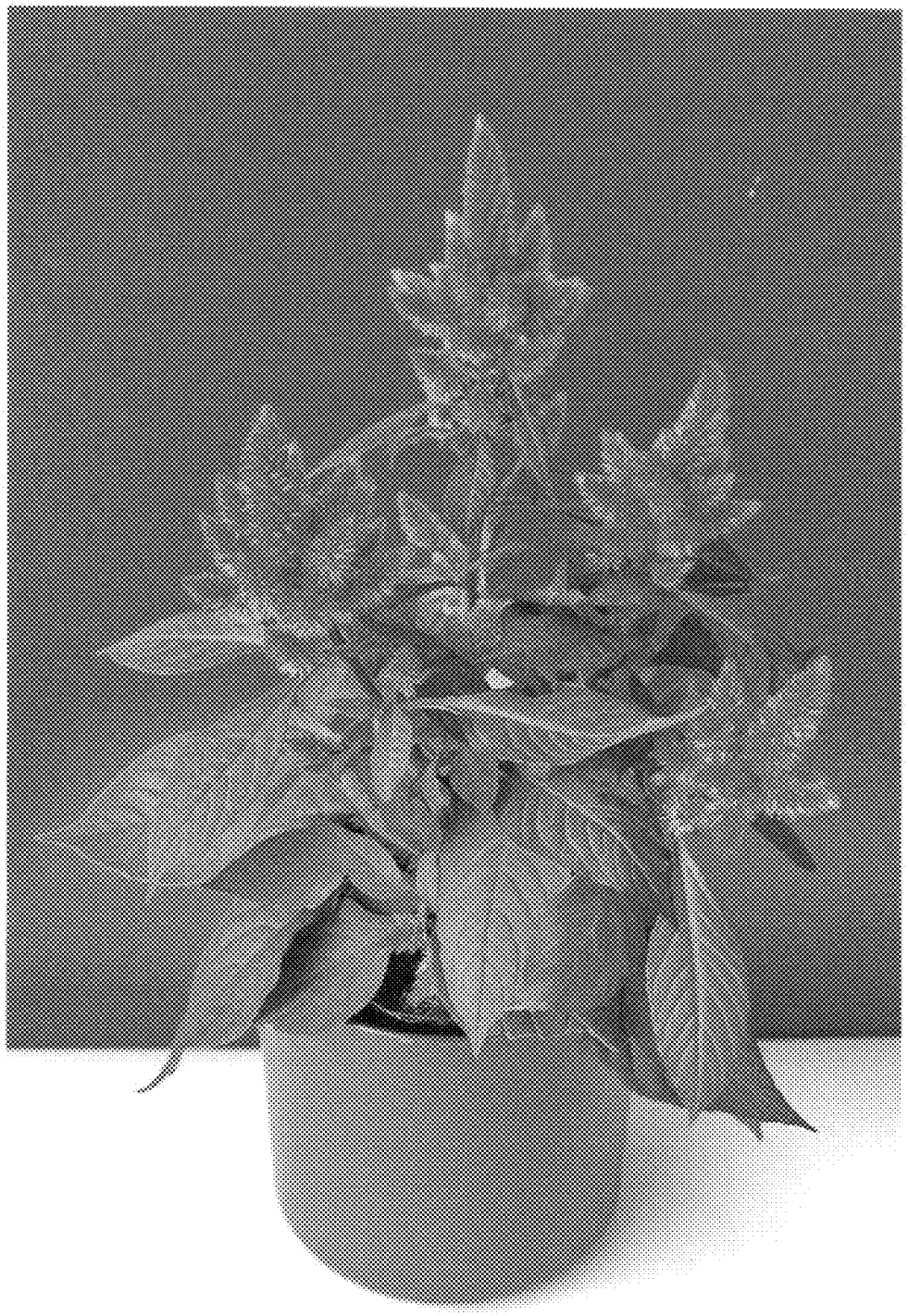

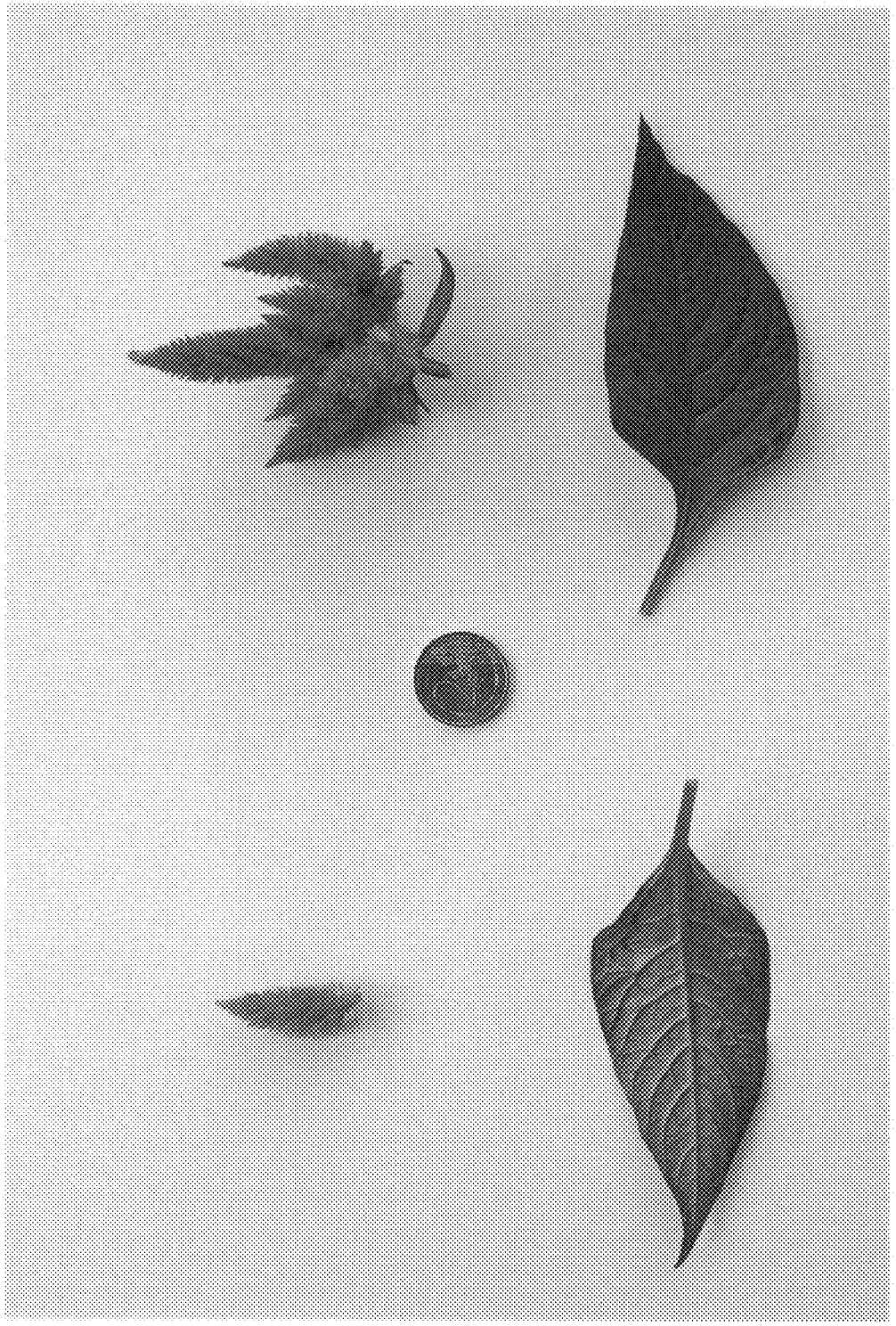

* * * * *